United States Patent [19]

Johnson et al.

[11] Patent Number: 5,356,809
[45] Date of Patent: Oct. 18, 1994

[54] PROCESSES FOR IN VIVO PRODUCTION OF ASTAXANTHIN AND PHAFFIA RHODOZYMA YEAST OF ENHANCED ASTAXANTHIN CONTENT

[75] Inventors: Eric A. Johnson, Madison, Wis.; Huei-hsiung Yang, Rockville, Md.; Beril Geldiay-Tuncer, Bostanli-Karsiyaka, Turkey; William T. Hall, Rockville, Md.; David Schreiber, Columbia, Md.; Kwok Ho, San Diego, Calif.

[73] Assignee: Igene Biotechnology, Inc., Columbia, Md.

[21] Appl. No.: 837,120

[22] Filed: Feb. 14, 1992

Related U.S. Application Data

[60] Division of Ser. No. 399,183, Aug. 23, 1989, which is a continuation of Ser. No. 385,961, Jul. 28, 1989, abandoned, which is a continuation-in-part of Ser. No. 229,536, Aug. 8, 1988, abandoned.

[51] Int. Cl.$^5$ .......................... C12N 1/16; C12P 23/00
[52] U.S. Cl. ........................ 435/255.1; 435/67; 435/244; 435/256.8; 435/911
[58] Field of Search .............. 435/255, 911, 67, 255.1, 435/244, 256.8

[56] References Cited

PUBLICATIONS

"ATCC Catalogue of Fungi/Yeasts" 17th ed. 1987 Jong et al. Editors.

Primary Examiner—Herbert J. Lilling
Attorney, Agent, or Firm—Sughrue, Mion, Zinn, Macpeak & Seas

[57] ABSTRACT

An economical process for in vivo production of the pigment astaxanthin, and particularly a process for enhancing astaxanthin content of cultures of microorganisms of genus Phaffia, the process comprising culturing a microorganism of genus Phaffia in a nutrient medium containing an antibiotic, a cytochrome B inhibitor, or a terpenoid synthetic pathway inhibitor, cultivating surviving pigment enhanced microorganisms, and harvesting the yeast.

4 Claims, 3 Drawing Sheets

PROCESSES FOR IN VIVO PRODUCTION OF ASTAXANTHIN AND PHAFFIA RHODOZYMA YEAST OF ENHANCED ASTAXANTHIN CONTENT

This is a divisional of application Ser. No. 07/399,183 filed Aug. 23, 1989, which is a continuation of application Ser. No. 07/385,961 filed Jul. 28, 1989, now abandoned, which is a continuation-in-part of application Ser. No. 07/229,536 filed Aug. 8, 1988, now abandoned.

FIELD OF THE INVENTION

The invention pertains in one aspect to an economical process for in vivo production of the pigment astaxanthin. In another aspect, the invention pertains to a process for enhancing astaxanthin content of cultures of microorganisms of genus Phaffia, the process comprising culturing a microorganism of genus Phaffia in a nutrient medium containing an antibiotic, a cytochrome B inhibitor, or a terpenoid synthetic pathway inhibitor, cultivating surviving pigment enhanced microorganisms, and harvesting the yeast.

BACKGROUND OF THE INVENTION

The reddish carotenoid pigment astaxanthin is commonly found in nature and is conspicuously displayed by a number of animals. Animals unable to synthesize this pigment rely on dietary intake of this pigment or a pigment precursor.

The red skin and flesh color of naturally occurring salmon and trout is due primarily to astaxanthin, which is usually present as an unbound pigment in these fishes. In nature, marine zooplankton and nekton in the diet provide salmon with their carotenoid pigments.

Due to a lack of dietary astaxanthin, fish raised on fish-farms or in hatcheries are generally pale and lack the skin and flesh colors characteristic of fish grown in their natural environment. Whether or not the carotenoids are nutritionally important in the animal or human diet has not been determined, but pigments do make certain foods attractive. That is, since the color of a food is frequently an indicator of its quality, there is a strong consumer preference for fish having natural coloration, even though nutritionally the pale farm produced fish may be identical to those grown in their natural environment. There is also evidence that astaxanthin or its precursor contributes to the distinctive flavor of baked salmon.

Recent increasing concern over health risks has resulted in a ban on various synthetic coloring agents which have a potential of carcinogenicity and/or teratogenicity. Yellow and red azo dyes which are increasingly prohibited from use in foods are being replaced with non-toxic carotenoids. The carotenoids are generally not toxic even at high levels. Thus, naturally occurring carotenoids are the preferred pigment for coloring, e.g., salmonids.

In the past, numerous studies have been carried out utilizing carotenoid containing crustaceans or crustacean processing wastes in salmonid diets. The pale color of fish produced on fish-farms or in hatcheries is improved when the fish are fed a diet supplemented by large quantities of dried, ground-up exoskeletal crustacean remains. Crustacean shells are, however, very low in carotenoid content and high in minerals which, without extensive processing to improve their dietary quality, restricts their inclusion in salmonid diets. Further, a satisfactory color can be developed in this manner of feeding only over long periods of time and it is desirable, if not indeed essential in the economic sense, to develop satisfactory colors within very short periods of time.

It is known that astaxanthin per se can be added to fish food to improve fish color. For example, U.S. Pat. No. 4,239,782 describes a method for enhancing the color of fish comprising adding to the fish food a pigmenting agent such as astaxanthin and additionally limited amounts of the hormone testosterone, which hormone acts as a catalyst in combination with a chosen pigmenting agent or agents to enhance the color of fish.

The two primary commercial sources for astaxanthin per se are extracts from crustacean shells and chemical synthetics. The red carotenoid pigment can be extracted from the exoskeletal crustacean shells and tissues and fed, admixed with other feed in dietary formulations, to the farm fish, crustacea and certain fowls in massive concentrations to develop satisfactory skin, flesh, carapace or egg yolk pigmentations. Examples of processes for extraction of astaxanthin from crustacean shell and tissue waste are described, for example, in U.S. Pat. Nos. 3,906,112 (Anderson) and 4,505,936 (Meyers et al).

In an article in *Journal of Food Science*, Volume 47 (1982), entitled "Extraction of Astaxanthin Pigment from Crawfish Waste Using a Soy Oil Process", various extraction techniques are described. For example, whole crawfish waste is ground-up, the comminuted crawfish waste is admixed with water, the pH is adjusted with an alkali or acid, an enzyme is added to the solution, and the solution stirred, heated and hydrolyzed. After hydrolysis, the astaxanthin is extracted with oil and the astaxanthin enriched oil recovered by centrifugation. However, the cost of natural isolates of astaxanthin, especially from krill and crawfish shells, can cost anywhere from $5,000 to $15,000 per kilogram. Obviously, a less source dependent and more economical process for production of astaxanthin is needed.

Pigmentation of salmon and trout flesh has also been accomplished using the synthetic carotenoid canthaxanthin as a feed additive, but this chemical is rather expensive and has been reported to produce a somewhat unsatisfactory color in salmonids. Recent work in chemical synthesis of astaxanthin is exemplified filed by U.S. Pat. Nos. 4,245,109 (Mayer et al), 4,283,559 (Broger et al), and 4,585,885 (Bernhard et al). The present cost of synthetic astaxanthin pigment is approximately $2,000 per kilogram. Many countries, however, prohibit the use of synthetic carotenoids.

Astaxanthin remains one of the most expensive ingredients used in salmon feed for pen-reared salmon. As the interest in aquaculture, i.e., farming fish, has exploded recently, the commercial demand for an economical source of astaxanthin has grown proportionately.

The pigmentation of avian egg yolks has also been studied because of the economic importance of color in chicken egg yolks. Yolks with a high pigment content are demanded. The most common pigment source in commercial diets has been yellow corn, which supplies the prominent egg yolk pigments cryptoxanthin, zeaxanthin and lutein. Unfortunately, higher energy grains such as milo, wheat, rice and barley are replacing corn in the chicken diet, with the consequent loss in pigmentation. Astaxanthin can be used as a poultry food supplement to increase yolk pigmentation.

One approach not presently commercially employed in production of astaxanthin is biosynthesis, i.e., employment of microorganisms to synthesize astaxanthin.

As a microbial source of astaxanthin, the yeast *Phaffia rhodozyma* is known (Johnson, "Astaxanthin Production by the Yeast *Phaffia rhodozyma* and its use as a Pigment Source in Animal Feeding", Masters Thesis, University of California at Davis, 1976). Yeast is generally considered to be a highly nutritious feedstuff and is often desirable in animal diets; the additional attribute of containing astaxanthin suggests that *P. rhodozyma* may be an ideal feed supplement for animals that require a dietary source of this pigment, e.g. salmonids, crustaceans, laying hens, or birds such as flamingoes.

However, the pigment yield of naturally occurring *P. rhodozyma* is only in the order of 200 to 600 ppm/dry weight of yeast in 6 day growth. As a source of astaxanthin per se, naturally occurring *P. rhodozyma* is inadequate. Experiments in supplementing the diets of certain fish, crustaceans and fowl with naturally occurring *P. rhodozyma* showed some promise. Practically, however, the large volume of *P. rhodozyma* which must be added as a food supplement in order to obtain satisfactory levels of pigmentation detracts from the commercial suitability of naturally occurring *P. rhodozyma* as a pigment source.

SUMMARY OF THE INVENTION

Accordingly, it is an object of the present invention to provide economical process for in vivo production of the pigment astaxanthin.

Another object of the present invention is to provide a process for obtaining cultures of the yeast *Phaffia rhodozyma* having increased astaxanthin content. Another object of the present invention is to provide *P. rhodozyma* characterized by a high astaxanthin content.

It is another object of the present invention to develop a process for improving astaxanthin content of progeny derived from naturally occurring *P. rhodozyma* such as strain ATCC-24230 or ATCC-24202 deposited with the ATCC.

Yet another object of the present invention is to develop a process for improving astaxanthin content of mutated strains of the yeast *P. rhodozyma*.

These and other objects have been attained by a process comprising, in it's most basic form, culturing a microorganism of genus Phaffia in a nutrient medium containing an antibiotic, a cytochrome B inhibitor, or a terpenoid synthetic pathway inhibitor, cultivating surviving pigment enhanced microorganisms, and harvesting the yeast.

The key step in strain development is the morphological selection step. There is no limit to the possible combinations of sequence and type of mutation and antibiotic, a cytochrome B inhibitor, or terpenoid inhibitor selection to which *P. rhodozyma* may be subject within the present invention. Recent results confirm the reproducibility of this technique.

Related objects and advantages of the present invention will become more apparent by reference to the following figures and detailed description.

BRIEF DESCRIPTION OF THE FIGURES

The process and apparatus in accordance with the present invention will be described with reference to the accompanying drawings, in which.

DETAILED DESCRIPTION OF THE INVENTION

During an expedition in 1967 for the purpose of studying yeast florae associated with trees on the major Japanese Islands and in the Pacific Northwest, a peculiar astaxanthin synthesizing organism was isolated from slime fluxes of various broad-leafed trees (Phaff et al., "A comparative study of the yeast florae associated with trees on the Japanese Islands and on the west coast of North America", Proc. IV: Ferment. Technol. Today, (1972) pp. 759–774). This organism, now known as *Phaffia rhodozyma*, was determined to have the capabilities of producing carotenoid pigments and fermenting several sugars.

Phaffia has been granted a genus because of its unique characteristics, which include its ability to ferment glucose and other sugars (compared to the other carotenoid-forming yeasts which are all strictly aerobic), its synthesis of astaxanthin as its principal carotenoid, its mode of bud formation, its possession of certain metabolic properties such as the ability to use urea which is less common in ascomycetous yeasts, and its cell wall composition. *P. rhodozyma*, the only species in this genus, reproduces exclusively by budding, and an examination of this mode of vegetative reproduction by scanning electron microscopy reveals that the yeast buds repeatedly from the same site which leads to the formation of the multilayered cell wall.

Other characteristics of Phaffia include its formation of chlamydospores, its mol % G+C content of 48.3%, its ability to split urea by urease, and its apparent lack of a perfect stage. Its properties suggest that the yeast is of basidiomycetous affinity. Attempts to find the sexual cycle of Phaffia have all failed.

Figure 1:
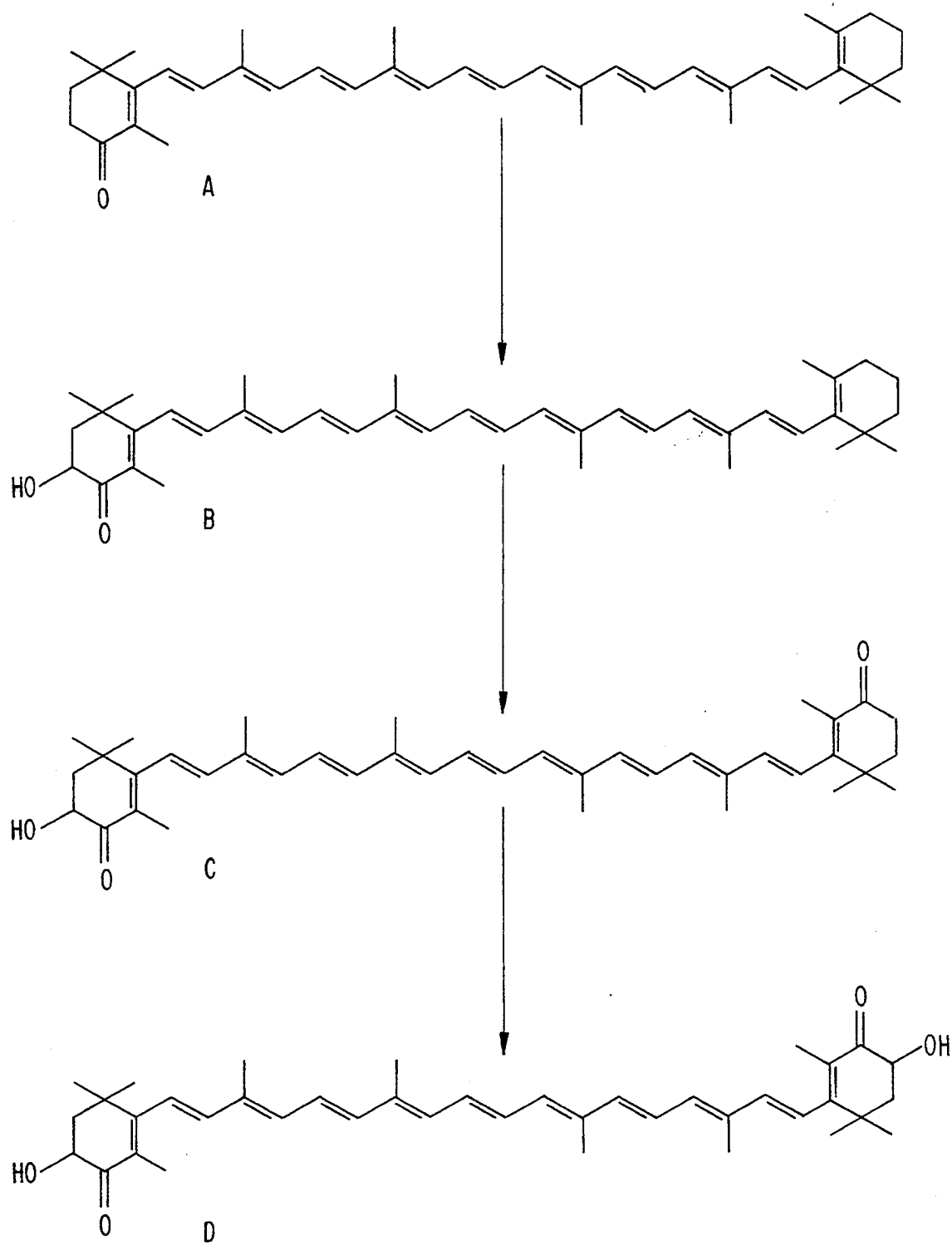
FIG. 1 shows the chemical structure and relationship of various pigments and intermediates found in *P. rhodozyma*.

Andrewes et al, as reported in "Carotenoids of *Phaffia rhodozyma*, a red pigmented fermenting yeast", Phytochem. 15, (1976) pp. 1003–1007, found the carotenoids of *P. rhodozyma* to be unusual. Pigments and pigment intermediates found by Andrewes in naturally occurring *P. rhodozyma* are shown in FIG. 1 where (A) is echinenone, (B) is 3-hydroxyechinenone, (C) is phenicoxanthin, and (D) is astaxanthin. Astaxanthin was found to be the major pigment synthesized by this yeast; in the naturally occurring yeast it comprised approximately 85% of the carotenoid mixture.

While the carotenoids of most plant and animal sources can be readily extracted with water-miscible solvents, the yeasts are well known for the tenacious attachment of their pigments. Astaxanthin is firmly attached in the yeast cell and not extractable by lipid solvents unless the structure of the yeast cell is first altered.

The most quantitative method of extraction involves mechanically breaking the yeast cells such as in a French press (Simpson et al., "Modified French press for the disruption of microorganisms", J. Bact., 86, (1963) pp. 1126–1127) or in a Braun homogenizer (Bae et al., "The occurrence of plectaniaxanthin in *Cryptococcus laurentii*", Phytochem., 10, (1970) pp. 625–629), and then extracting the cells with solvents. These methods are used routinely for estimation of astaxanthin concentration.

The need for the large scale recovery of astaxanthin led to the development of an enzymatic method of extraction. The method utilized extracellular lytic enzymes produced by the bacterium *Bacillus circulans* WL-12, which partially digested the yeast cell wall and rendered the carotenoid pigments extractable by lipid solvents. Complete extraction of astaxanthin from heat-killed *P. rhodozyma* cells was obtained after growing *B. circulans* WL-12 on these yeast cells for 26 hours and then extracting the yeast-bacterium mixture with acetone.

A bacteria-free lytic system, which gave quantitative extraction of astaxanthin from *P. rhodozyma*, was obtained by concentrating the culture broth from the growth of *B. circulans* WL-12 on *P. rhodozyma* cells. Preferably, *B. circulans* WL-12 is grown on a medium containing *P. rhodozyma* cells. The lytic system was found to work most efficiently at pH 6.5 and with low concentrations of yeast.

Generally, nutrition and environment have an effect on carotenoid yield in various carotenoid producing microorganisms. Enhancement of carotenoid formation in fermentations in complex media has been reviewed (Hanson, "Microbial production of pigments and vitamins", in Microbial Technology, edited by H. J. Peppler, Reinhold, N.Y., (1967) pp. 222–250).

Carotenoids are tetraterpenes and their basic pathway of synthesis is similar to that of other terpenoids. Acetyl CoA is the initial precursor and the first specific terpenoid compound is mevalonic acid (Schopfer et al, "Sur la biosynthése du β-caroténe par Phycomyes cultivé sur un mileu contenant de l'acétate de sodium comme unique source de carbone", Experientia, 8, (1952) p. 140). Isopentenyl pyrophosphate is the fundamental precursor from which carotenoids are derived (see Goodwin, "Biosynthesis", Carotenoids, Edited by O. Isler, Basel, Birkhauser, (1971) pp. 577–636; Britton, "Biosynthesis of Carotenoids", in Chemistry and biochemistry of plant pigments, Vol. 1, (1976) pp. 262–327).

Most previous work with *P. rhodozyma* has been done with the type strain #67-210. Visual examination of young colonies of several additional natural isolates (UCD-FST #s 67-202, 67-203, 67-210, 67-383, 67-385 and 68-653C) indicated that 67-210 and 67-385 (American Type Culture Collection ATCC Nos. 24202 and 24230 respectively) were the most highly pigmented strains. Quantitative determination of astaxanthin content in these two strains after 5 days growth in YM broth indicated that 67-385 contained ≈450 μg/g dry yeast in comparison with ≈295 μg/g in 67-210. 67-385 was primarily employed by the inventors for strain development because of its higher natural astaxanthin content.

As a result of a series of experiments designed to determine the optimal culture conditions for growth and pigmentation of *P. rhodozyma*, it was found that astaxanthin biosynthesis occurred maximally during the exponential phase of growth. The pigment yield in the growth medium was found not to be solely dependent on cell concentration but was influenced by the culture conditions. The optimal pH for astaxanthin production was found to be 5.0 in shake flasks. At the other pHs tested, however, the concentration of astaxanthin in *P. rhodozyma* remained relatively constant.

The temperature of cultivation was found to influence the growth rate of *P. rhodozyma* but not the accumulation of astaxanthin in the yeast cell. The effects of light also did not affect carotenogenesis in *P. rhodozyma*, although the cells grown under high light intensity appeared to have a redder hue, which may have been due to different concentrations of particular carotenoids.

It was found that a low glucose concentration and high air supply promoted efficient astaxanthin production by *P. rhodozyma*. The concentration of astaxanthin in the red yeast decreased considerably if the air supply was below 20 mmoles/h or the glucose concentration was above 4% w/v. However, astaxanthin was still the predominant pigment in yeast cultured under either of these conditions. If the effects of low air and high glucose were combined, however, then the astaxanthin concentration in *P. rhodozyma* was decreased to extremely low levels and the formation of β-zeacarotene occurred. Under these adverse conditions, again, astaxanthin was not efficiently formed from the carotenes.

When cultured on carbon compounds which repressed ethanol production in this yeast (e.g. cellobiose) the yields of astaxanthin were comparatively high. If cultured on carbon sources which presumably promoted ethanol production (e.g. high glucose) the astaxanthin yields were comparatively low. Carbon compounds metabolized via the pentose-phosphate pathway (e.g. xylose) did not promote efficient carotenogenesis.

Despite extensive experimenting in optimizations of nutrient medium and environmental conditions on naturally occurring strains of *P. rhodozyma*, a dramatic increase in pigment content was not attained. The inventors concluded that manipulation of the above discussed factors alone may not be sufficient to induce increase in astaxanthin content of *P. rhodozyma* to the extent necessary to render biosynthesis commercially feasible.

With the objective of isolating a novel genetic mutant of *P. rhodozyma* capable of increased astaxanthin production, *P. rhodozyma* was subject to mutagenesis. However, results were inconsistent, presumably due to the random and non-directed nature of mutation. For example, attempts at isolating highly pigmented variants were not successful after screening several thousand colonies after UV exposure. Most of the UV-generated mutants were considerably reduced in astaxanthin content and were very pale.

Potential for further progress in improvement in astaxanthin content in *P. rhodozyma* by conventional mutagenic techniques appears to be limited. This is because microorganisms possess tight genetic regulatory controls over the biosynthesis of their cellular components so that they tend not to overproduce unnecessary cellular constituents. Since the biosynthesis of pigment such as astaxanthin is apparently tightly regulated in any given strain of yeast cells, the chances of producing a viable inheritable genetic alteration to produce colonies capable of increased astaxanthin production by undirected mutagenesis is probably very low.

Since screening of colonies after mutagenesis was relatively unsuccessful, the inventors tried to develop selection procedures for astaxanthin overproduction. Because astaxanthin formation is decreased by high concentrations of glucose, the inventors tried 2-deoxyglucose as a selective agent to isolate glucose-resistant strains that might be catabolite-derepressed and, in turn, exhibit enhanced pigment biosynthesis. Although some strains generated by this selective procedure were changed in pigmentation, many were extremely unstable and none were increased in astaxanthin concentration more than two-fold over the naturally occurring parent.

Inhibitors of sterol biosynthesis including ketoconazole and miconazole were incorporated into yeast malt extract medium agar, which resulted in significant killing of *P. rhodozyma*. Screening of several thousand survivors, however, did not produce highly pigmented yeast strains. Several other compounds tested including nicotine (1 mM), imidazole (4 mM), 2-methylimidazole (1 mM), and morpholine (10 mM) did visually change the color of the colonies, but did not impair growth, which indicated a change in carotenoid composition. However, since these variants were not increased in astaxanthin, no further analysis in the changes in pigment compositions was carried out.

The inventors also tried treating *P. rhodozyma* with several inhibitors of electron transport including thenoyltrifluoroacetone (TTFA), antimycin A, and sodium cyanide. Naturally occurring *P. rhodozyma* was substantially killed by low concentrations of antimycin A and TTFA, but was found to be relatively insensitive to cyanide and azide.

As a result of extensive experimentation, discussed above in part, the inventors made a surprising discovery of a process by which colonies of *P. rhodozyma* can be produced, which colonies are characterized by a high astaxanthin content. *P. rhodozyma* produced by the process of the present invention is non-reverting, the astaxanthin is present in the yeast in a sufficiently high concentration to be a more effective dietary food and pigment supplement than naturally occurring *P. rhodozyma*, and colonies of the yeast can be obtained which are able to produce astaxanthin in sufficient quantities to render astaxanthin fermentation a commercially feasible process for production of astaxanthin.

More specifically, the inventors have discovered that by subjecting a naturally occurring or mutated strain of *P. rhodozyma* to growth in the presence of a metabolic pathway inhibitor, particularly a main respiratory pathway inhibitor, in the presence of an influence such as an agent or environmental condition which triggers a secondary respiratory pathway, or morphological selection using a selecting agent, and particularly an antibiotic, a cytochrome B inhibitor, or a terpenoid synthetic pathway inhibitor as a selecting agent, a directed and specific selection of highly pigmented *P. rhodozyma* takes place. For example, plating of the pink yeast, *P. rhodozyma*, to agar containing an antibiotic, a cytochrome B inhibitor, or a terpenoid synthetic pathway inhibitor gave rise to colonies of unusual morphology characterized by a nonpigmented lower smooth surface that developed highly pigmented vertical papillae after 1 to 2 months. Isolation and purification of the papillae, followed by testing for pigmentation in shake flasks, demonstrated that several mutans were increased 3 to 6 fold in astaxanthin content compared to the parental natural isolate.

One of the selected progeny (IGI-887J0; see FIG. 2 and accompanying text) was characterized physiologically. The mutant grew slower on various nitrogen sources and had lower cell yields on several carbon sources. It showed increased sensitivities to the respiratory inhibitors such as antimycin A and TTFA, but did not differ from the natural isolate in sensitivity to cyanide or azide. It was more sensitive to killing by hydrogen peroxide. Analysis of the carotenoids by thin layer chromatography showed two unknown carotenoids not present in the parent, as well as an increased accumulation of carotenes and cis-astaxanthin.

Antibiotic selection agents include, for example, one or more of antimycin, tunicamycin and nystatin. Antimycin may also be classified as an electron transport inhibitor or a cytochrome B inhibitor. Other cytochrome B inhibitors which enhance pigmentation of select progeny include, for example, 2-n-heptyl-4-hydroxy-quinoline-N-oxide (HOQNO). The terpenoid synthetic pathway inhibitors include, for example, mevalonic acid lactone, which may be generally referred to as a metabolic inhibitor, and which is an example of a sterol inhibitor.

Concentrations of selection agents, e.g., antimycin, preferably range from 1 to 100 $\mu$M on yeast malt extract medium (YM) plates, more preferably 30 to 80 $\mu$M, and most preferably, for generation of the most distinctive colonies, are approximately 50 $\mu$M.

The effect of the antibiotic, cytochrome B inhibitor, or terpenoid synthetic pathway inhibitor on *P. rhodozyma* is surprising and the specific underlying mechanism has yet to be elucidated. It is surprising that *P. rhodozyma* subjected to antibiotic, cytochrome B inhibitor, or terpenoid synthetic pathway inhibitor selection produce colonies of higher pigment contents, while experiments conducted with other agents, such as respiratory inhibitors including KCN, rotenone, TTFA and others, do not seem to significantly influence pigmentation of *P. rhodozyma* on YM plates or in liquid growth media.

The inventors have developed a hypothesis which may provide a possible explanation for the effect of antimycin on *P. rhodozyma*, but this hypothesis is speculative and should not be taken to effect the scope of the invention.

The inventors suspect that since ring closing and hydroxylation may depend on cytochrome P450 as occurs in sterol synthesis, and a cytochrome B inhibitor such as antimycin reacts with cytochrome B which is the same cytochrome that reduces cyt. P450, perhaps the increased pigmentation in the antimycin mutants is due to altered cyt. P450 function or activity. Also this molecule is known to inactivate glutamine synthetase and this may be the reason for an observed slowing of nitrogen catabolism. A further discussion of the hypothesis can be found in An et al, "Isolation of Mutants of *Phaffia rhodozyma* with increased quantities of Astaxanthin", unpublished manuscript, authored in significant part by a co-inventor, a copy of which is provided herewith.

Recent results confirm that this technique can work repeatedly with *P. rhodozyma*.

The naturally occurring or antibiotic, cytochrome B inhibitor, or terpenoid synthetic pathway inhibitor selected yeast cells may additionally be exposed to a mutagen before, after, or before and after selection, or in any desired number or combination of mutation and selection steps, so long as antibiotic, cytochrome B inhibitor, or terpenoid synthetic pathway inhibitor selection is included in the protocol.

Mutagens or mutagenic agents can be selected from a variety of chemicals or other exposures, and are preferably powerful enough to cause production of nonrevertable mutations. Mutants wherein no degeneration has been observed are highly desirable for industrial uses. Strong mutagens include ethylmethane sulfonate, nitrosoguanidine (N-methyl-N-nitro-N-nitroso-quanidine), nitrous acid (though relatively high amounts may be needed), ultraviolet radiation in significant amounts, x-ray, and others.

Presently preferred are nitrosoquanidine and UV because of their ready availability, their relatively powerful mutagenic nature, and their relative ease and safety of handling. However, any strong mutagen can be employed, using amounts and exposure techniques as known in the art.

In some cases a weak mutagen can be combined with a strong mutagen. Among the weak mutagens are 2-aminopurine, t-bromouracil, hydroxylamine, sodium bisulfite, and others.

Figure 2:
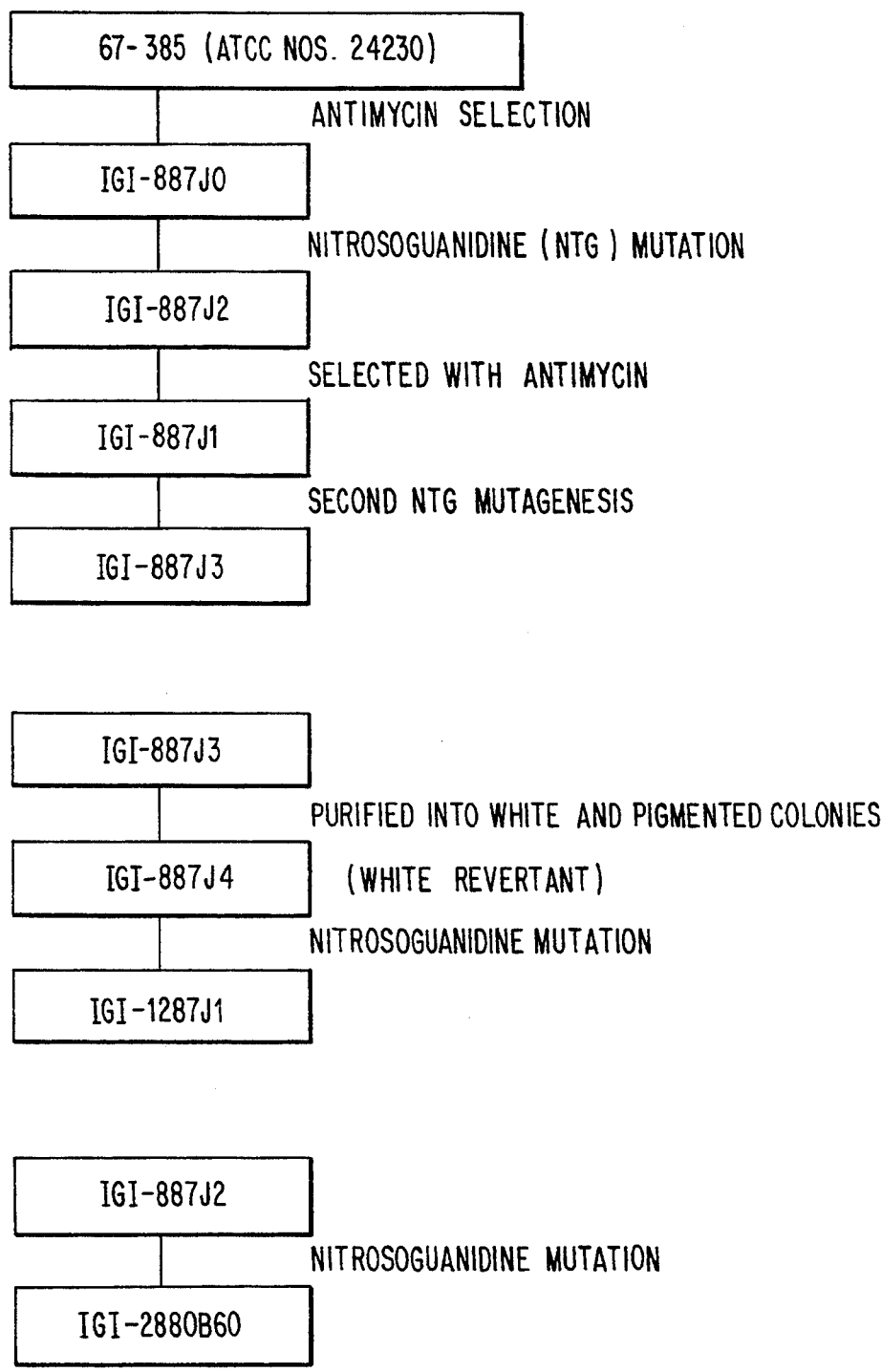
FIG. 2 is a flow chart showing preferred sequences of mutant isolations in *P. rhodozyma*.
Figure 3A:
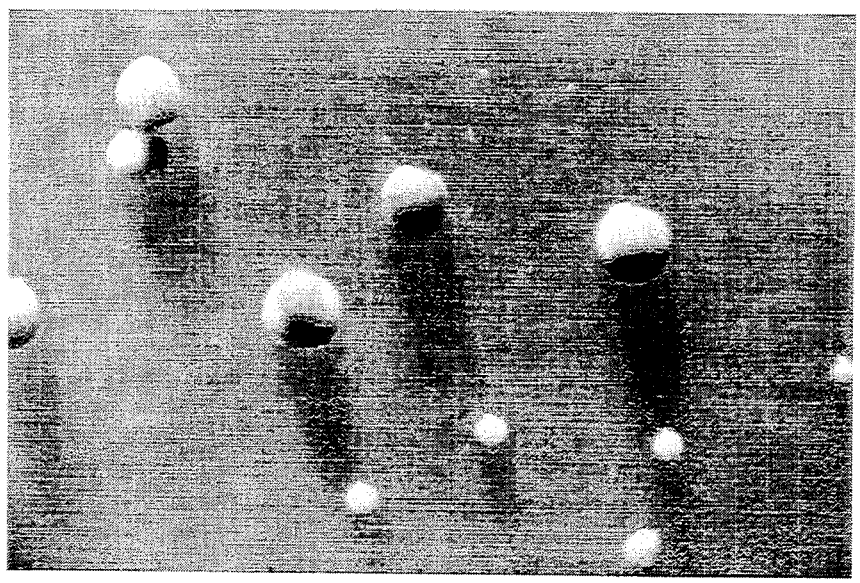
FIGS. 3A and 3B are photomicrographs showing the appearance of variegated colonies.
Figure 3B:
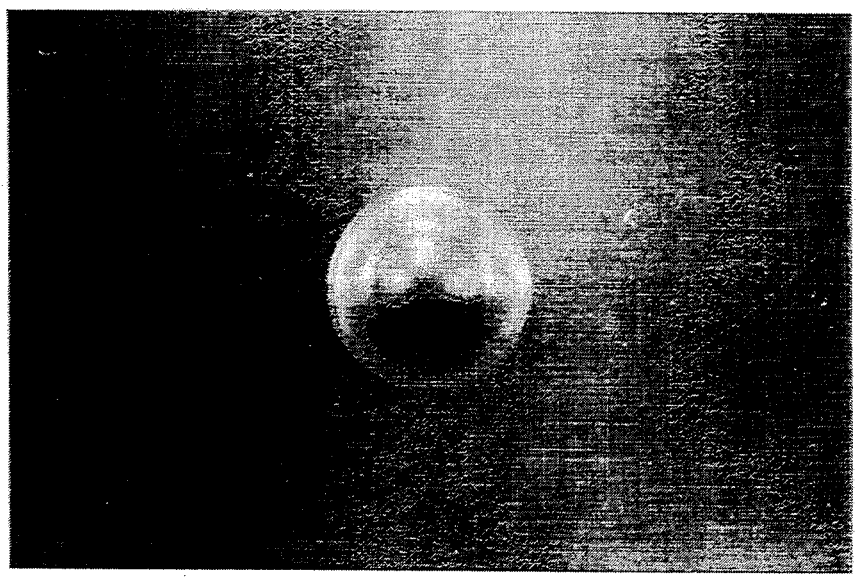

The sequence of mutations and selections with which the highest astaxanthin yielding strains to date have been produced is shown in FIG. 2. With reference to FIG. 2, the naturally occurring parent 67-385, obtained from the American Type Culture Collection ATCC No. 24230, was assayed as containing 200–600 $\mu g/g$ dry weight of yeast in 6 day growth. 67-385 was subjected to antimycin selection, and higher pigmented progeny, referred to as IGI-887J0 were obtained. The first mutant papillus dissected from the basal colony contained approx. 700 $\mu g$ total carotenoid/g yeast compared to the parental strain which had 300 to 400 $\mu g/g$. IGI-887J0 was assayed to have an astaxanthin content of 960 $\mu g/g$ dry weight of yeast in 6 day growth. IGI-887J0 was replated to YM agar containing 50 $\mu M$ antimycin and second generation antimycin colonies were selected. One of these produced 1200 $\mu g/g$ and another produced 1450 $\mu g/g$. Therefore, it appeared that antimycin A is an excellent selective agent for isolating pigmented variants of P. rhodozyma.

IGI-887J0 were subject to nitrosoquanidine (NTG) mutation and IGI-887J2 were obtained which produced 1200 to 1500 $\mu g$ total carotenoids/g yeast. IGI-887J2 were further selected with antimycin to produce IGI-887J1 which was assayed to have an astaxanthin content of 700–1100 $\mu g/g$ dry weight of yeast in 6 day growth. A second NTG mutagenesis produced IGI-887J3 progeny. IGI-887J0 and IGI-887J2 were deposited at the American Type Culture Collection, Rockville Md. on Jun. 13, 1989 under accession numbers 66270 and 66272, respectively.

Upon purification of colonies of IGI-887J3 the isolates segregated into white and pigmented colonies. The white revertant was designated IGI-887J4. The pale colonies grew very poorly on ammonium sulfate at 5 g/l, grew a little better on high levels of ammonium sulfate (20 g/l), and on plates grew well on glutamate or glutamine. These results suggest that the strains are progressively impaired in nitrogen metabolism which limits growth rate.

IGI-1287J1 was isolated after nitrosoguanidine mutation of IGI-887J4, the white segregant of IGI-1887J3. IGI-1287J1 was assayed as containing 900–1400 $\mu g/g$ dry weight of yeast in 6 day growth. This strain also was impaired in nitrogen metabolism. It was noted that strains IGI-887J3 and IGI-1287J1 do not grown on ethanol, while the prior mutants do.

IGI-2880B60 was obtained from IGI-887J2 by NTG mutagenesis, and was assayed to contain 1700 $\mu g/g$ dry weight of yeast in 6 day growth.

Characterization of the Antimycin Mutants

The parental strain (67-385), IGI-887J0, and IGI-887J2 had approximately equal yields of cells with ammonium, glutamate or glutamine as nitrogen sources. However, analysis of growth rates showed that the series of strains grew progressively slower on these nitrogen compounds. These data suggested that the rate or efficiency of nitrogen utilization was impaired in the antimycin mutants.

The parent and two studied mutants had reduced cell yields on four carbon sources tested, but were more highly pigmented. The antimycin mutants still fermented glucose and also had significant ethanol dehydrogenase activity. However, IGI-887J2 no longer grew on ethanol and had reduced cell yields on other respiratory substrates including succinate. The reduced yields on the energy sources and the specificity of inhibition by antimycin for the electron transport chain suggested that respiration or mitochondrial function in the pigmented mutants was altered.

Sensitivities of the mutants to various respiratory inhibitors including antimycin A, theonyltrifluoroacetine, sodium azide, hydrogen peroxide and sodium cyanide were examined. These inhibitors affect different regions of the respiratory chain. Surprisingly, the antimycin-induced mutants were more sensitive to antimycin A on YM plates and also in liquid media. The parental strain had approximately 50% survival at 100 $\mu M$ antimycin, compared to the mutants which did not survive about 60 $\mu M$. The concentrations of antimycin that killed 50% of the populations of IGI-887J0 and IGI-887J2 on YM agar were approximately 18 and 3 $\mu M$, respectively. The mutants were more sensitive in liquid media and were killed at antimycin concentrations near 0.5 $\mu M$.

These results clearly show that the pigmented papillae that arose from the pale colonies were actually more sensitive to the drug even though they were isolated on plates containing antimycin. Apparently, the spatial separation of the papillae from the agar facilitated the generation of the more sensitive strains.

The mutants were also quite sensitive to other respiratory inhibitors including TTFA and hydrogen peroxide, but were only slightly more sensitive to cyanide, and did not differ in sensitivity to azide. These data supported the above hypothesis that the antimycin-isolated strains possessed an altered respiratory chain, and suggested that a lesion may occur in the early regions of the chain, near cytochrome b.

For carotenoid composition of mutants, see An et al, "Isolation of Mutants of *Phaffia rhodozyma* with increased quantities of Astaxanthin", unpublished manuscript, authored in significant part by a co-inventor, a copy of which is provided herewith.

It is necessary to supply suitable amounts of nutrients and minerals in the feed media in order to assure proper microorganism growth, to maximize assimilation of the carbon energy source by the cells in the microbial conversion process, and to achieve maximum cellular yields with maximum cell density in the fermentation media.

The composition of the ferment can vary over a wide range, depending in part on the yeast strain, the substrate employed, and the minerals content in the ferment (that is, liquid plus cells). Set forth in the table below are the minimum, broad, and presently preferred ranges of concentrations of various elements in the ferment, the concentration being expressed as of the element, though it is recognized that all or part of each can be present in the form of a soluble ion, or in cases such as P, in a combined form of some type such as phosphate. The amount of each element is expressed in grams or milligrams per liter of ferment (aqueous phase, including cells):

| Element | Weight of Element per Liter of Ferment | | |
|---|---|---|---|
| | Minimum | Broad Range | Preferred Range |
| P | 0.2 g | 0.2–5 g | 0.4–2 g |
| K | 0.1 g | 0.1–3 g | 0.1.0.7 g |
| Mg | 0.15 g | 0.15–3 g | 0.3–1.2 g |
| Ca | 0.06 g | 0.06–1.6 g | 0.08–0.8 g |
| S | 0.1 g | 0.1–8 g | 0.2–5 g |
| Fe | 0.5 mg | 0.5–30 mg | 0.6–20 mg |
| Zn | 2 mg | 2–100 mg | 3–40 mg |
| Cu | 0.6 mg | 0.6–16 mg | 1–10 mg |
| Mn | 0.6 mg | 0.6–20 mg | 0.9–8 mg |

The manner in which to carry out the present invention, and further features and advantages of the present invention, will be apparent from the following illustrative Examples. The Examples are provided for the purpose of promoting an understanding of the principles of the invention. Although the conditions and language in the examples is specific, it will nevertheless be understood that no limitation of the scope of the invention is thereby intended, such alterations and further modifications and applications of the basic principles of the present invention as illustrated therein being contemplated as would normally occur to one of ordinary skilled in the art to which the invention relates.

In the Examples, naturally occurring strains are obtained from the official depository, the American Type Culture Collection in Rockville, Md., and given ATCC Nos. 24230 and 24202. The ATCC designations reflect that two agar slant cultures of each strain have been deposited with the official depository.

Mutagenesis

EXAMPLE 1

Ultraviolet Mutagenesis

Strain IGI 2880B60 was mutagenized with ultra-violet light from a germicidal UV lamp at a distance of 12 inches from a saline suspension of cells for 1 min. (95.3% kill), 3 min. (99.4% kill), and 5 min (99.99% kill). Mutagenized cells were kept in the dark for 1 hr. following the period of mutagenesis and plated on yeast malt extract medium (YM) at several dilutions. Plates were incubated at 20° C. Dark red orange colonies were isolated on the basis of observed pigmentation differences and streaked to slants.

EXAMPLE 2

Nitrosoguanidine Mutagenesis

Stain 1287J1 was grown in YM for 48 hr. Cells were pelleted by centrifugation, the supernatant discarded, and the cells resuspended in 0.1M citrate buffer, pH 5.0. Cells were treated with 100 µg/ml nitrosoguanidine (NTG) for 25 min. at room temperature without shaking. The suspensions were centrifuged, the supernatant decontaminated, and the cells were washed three times with 0.1M potassium phosphate buffer, pH 7.0. Pellet was suspended in phosphate buffer and diluted into flasks containing 20 ml YM and shaken overnight. Cells were plated on YM and incubated at 20° C. Colonies were isolated on the basis of observed pigmentation differences, with the colonies characterized by dark reddish orange as observed under a dissecting microscope being selected, and streaked to slants. Three day old slants were used to inoculate YM flasks. One ml of YM medium was used to suspend the contents of the slant and this entire suspension was added to 250 ml flasks containing 20 ml YM and shaken for 6 days at 20° C.

Morphological Selection

EXAMPLE 3

Antimycin Treatment

Exponentially growing yeast cells of strain ATCC 24230, either NTG mutagenized as described under Step 1(a) above or non-mutagenized, were plated on YM medium containing 50 µm antimycin A (a mixture of antimycins $A_1$ and $A_3$; Sigma catalog #2006) and incubated at 20° C. until a colony grew. Growth took approximately one month. After two more weeks of incubation a red center appeared in the colony presenting a fried egg appearance. This red center was isolated to YM medium.

EXAMPLE 4

Tunicamycin Treatment

Tunicamycin mutants were selected by plating a log phase culture of strain ATCC 24202 (naturally occurring) on a gradient plate of GYE agar with 5 µg/ml tunicamycin. Colonies which grew on these plates were streaked to GYE agar plates containing 5 and 8 µg/ml tunicamycin. Colonies which grew on these secondary plates were assayed for pigment. Control was 270 µg/g as compared to 610 µg/g for 8 µg/ml tunicamycin resistant mutant.

EXAMPLE 5

Nystatin Treatment

Nystatin mutants were isolated by inoculating log phase YM cultures of strain ATCC 24202 into YM flasks containing 3 and 5 µg/ml nystatin. After 48 hours, these selective cultures were plated to antibiotic plates containing YM agar with nystatin (3 and 5 µg/ml). Colonies obtained were assayed for pigment. Control was 270 µg/g as compared to 400 µg/g for highest nystatin mutant.

EXAMPLE 6

Mevalonic Acid Treatment

Strain ATCC 24202 was mutagenized with NTG to 50% survival and plated to YM medium. Colonies were randomly plated to YM agar containing 5 mM mevalonic acid lactone. All of these colonies were subsequently transferred to medium containing first 10 and then 25 mM mevalonic acid lactone. Colonies which grew on 25 mM mevalonic acid lactone were assayed for pigment. Control was 275 µg/g as compared to 540 µg/g for 25 mM mevalonic acid lactone resistant mutant.

Carotenoid Extraction and Analysis

Colonies may be analyzed for pigment content as follows.

After harvest from 30 ml growth medium, the cells are washed in water and resuspended in 30 ml of water. The optical density is measured to determine growth. Approx. 13 ml of the suspension is broken with 0.5 mm glass beads for 3 to 4 minutes with cooling within a Bead Beater (Bio Spec Products, Bartlesville, Okla.). After breakage, the bead/cell mixture is poured into a beaker and extracted 5× with 10 ml aliquots of acetone. The acetone extracts are pooled and centrifuged at 15,000 rpm for 45 min. The clear acetone supernatant is poured off the cell pellet; if the pellet contains residual pigment, it is manually ground with a glass homogenizer and further extracted with acetone.

The combined acetone extracts are combined in a separatory funnel, and approximately 10 ml of petroleum ether is added as well as a few ml of a solution of saturate NaCl to help break the emulsion. The petrol extract is collected and the acetone layer is re-extracted. The petrol extracts are combined and filtered through glass wool to remove lipid globules and other particulate matter. The absorbance spectrum is recorded (the absorbance maximum of transastaxanthin in petroleum ether is 474 nm). The total carotenoid composition is calculated using the 1% extinction coefficient=2100 by the formula:

Total carotenoid (μg/g yeast) =

$$\frac{(ml\ petrol)\ (absorbance\ 474\ nm)\ (100)}{(21)\ (dry\ weight\ yeast\ [g])}$$

Individual carotenoids may be analyzed by thin layer chromatography (TLC) and electronic absorption spectra. To prepare carotenoid extracts for analysis, petroleum ether extracts are dried over anhydrous $Na_2SO_4$ and concentrated by evaporation in a stream of nitrogen. These are chromatographed by TLC on silica gel plates (Silica gel 60, 5×20 dm, 0.25 mm thickness (E. Merck, Darmstadt, West Germany) using 20% acetone/80% petroleum ether. After development, bands are scraped and eluted in acetone through a Pasteur pipet plugged with glass wool. Absorbance maxima, $r_f$ values, and cochromatography with standards are used for identification of the pigments. Visible absorption spectra are recorded in acetone or petrol on a Gilford Response spectrophotometer, and concentrations of carotenoids are calculated using the specific absorption coefficients listed by Davies, Carotenoids, p. 38–165, in Chemistry and Biochemistry of Plant Pigments, vol. 2., T. W. Goodwin (ed.), Academic Press, London (1976).

Bench Scale Fermentation

EXAMPLE 7

The production of astaxanthin in a 10 liter laboratory fermenter is illustrated by the following procedure:

20 ml. of frozen *Phaffia rhodozyma* strain IGI-887J1 (see FIG. 1 and accompanying text) was used to inoculate 300 ml of a medium comprising 3% glucose, 1% yeast extract and 0.1% caesin hydrolysate. The medium was sterilized at 121° C. and 15 p.s.i. for about 20 minutes before being inoculated. The inoculated medium was shaken for ≈48 hours at a temperature of 20° C. on a rotary shaker with a 1 inch stroke at a speed of 250 r.p.m. The 300 ml cell broth was used to inoculate a 5 liter seed fermenter, containing 3 liters of sterilized seed medium having the following composition per liter:

|  | G |
|---|---|
| Ammonium sulphate | 5.0 |
| Potassium phosphate monobasic | 1.5 |
| Magnesium sulphate heptahydrate | 1.5 |
| Calcium chloride dehydrate | 0.1 |
| Yeast extract | 6.0 |
| Vitamin mixture | 2 ml |

-continued

|  | G |
|---|---|
| Trace element mixture | 1 ml |

The vitamin mixture consists of the following ingredients:

|  | G |
|---|---|
| Biotin | 0.08 |
| Inositol | 5.00 |
| Thiamine | 5.00 |
| Calcium Pantothenate | 1.00 |
| Pyroxidine HCL | 2.25 |
| Water, q.s. to make 1 L | |

The trace element mixture consists of the following ingredients:

|  | G |
|---|---|
| 1) $FeCl_3.gH_2O$ | 3 |
| 2) $Na_2MoO_4.2H_2O$ | 2 |
| 3) $ZnSO_4.7H_2O$ | 8 |
| $MnSO_4.H_2O$ | 3 |
| $CuSO_4.5H_2O$ | 6 |
| Water, q.s. to make 1 L | |

After inoculation, a 70% cerelose solution was fed incrementally to the fermenter, specific growth rate of the cells was kept at about u=0.15. The fermenter was maintained at a temperature of 20° C. pH was controlled at 5 with 8N KOH. Agitation was at the rate of 900 r.p.m. and aeration was at the rate of 1.5 v/v/m. When $OD_{660}$ (optical density) was about 30, 1 L of the broth was used to inoculate a 15 liter fermenter containing 10 liter of production medium.

The composition of the production medium was the same as the seed medium except: (1) ammonium sulphate was increased to 16 g/L, and (2) 1 g/L monosodium glutamate and 5 g/L corn steep liquor was added. The fermenter temperature was maintained at 20° C. and pH was maintained at 5 with 8N KOH. Agitation and aeration was at the rate of 900 r.p.m. and 1.5 v/v/m respectively. About 2 liter of 70% cerelose was fed incrementally to the fermenter, specific growth rate of cells was kept below 0.15. At the end of the fermentation (about 60 hrs), the cells contained about 1100 ug/g astaxanthin.

Scale-Up Fermentation

EXAMPLE 8

The production of astaxanthin on a pilot plant scale is illustrated by the following procedure.

20 ml of frozen *P. rhodozyma* strain IGI 188JB1 (see FIG. 1 and accompanying text) was used to inoculate 300 ml of growth medium, the composition of the medium and culture conditions was the same as described in Example 1. After 48 hours, the 300 ml cell broth was used to inoculate the first seed fermenter, containing 3 liter of a sterilized first seed medium having the following composition per liter:

|  | G |
|---|---|
| Ammonium sulphate | 4.0 |
| Potassium phosphate monobasic | 1.5 |
| Magnesium sulphate heptahydrate | 1.5 |

-continued

|  | G |
|---|---|
| Calcium chloride dehydrate | 0.1 |
| Yeast extract | 4.0 |
| Corn steep liquor | 10.0 |
| Vitamin mixture | 2 ml |
| Trace element mixture | 1 ml |

*same as in Example 1

90 g of sterilized cerelose was added aseptically to the fermenter after inoculation. The fermenter was maintained at 21° C., pH was controlled at 5 with 8N KOH. Agitation was set at 900 r.p.m. and aeration was at 1.5 v/v/m. When the initial cerelose was used up, a sterilized 70% cerelose solution was incrementally fed to the fermenter. The specific growth rate of the cells was controlled at about 0.1. When cell growth reached an O.D. of about 20, the 3 liter cell broth was used to inoculate a 30 liter fermenter containing 20 liter of sterilized 2nd stage seed medium.

The composition of 2nd stage seed medium was the same as the 1st stage seed medium. Culture conditions were also the same with the exception of a slower, 300 r.p.m. agitation rate. When the initial cerelose was exhausted, a sterilized 70% cerelose, 7% ammonium sulphate solution was incrementally fed to the fermenter until an O.D. of about 30 was reached. The specific growth rate of the cells was controlled at about 0.1. The 2nd seed was used to inoculate a 250 liter fermenter containing 170 liter of sterilized production medium.

Except for a higher concentration of corn steep liquor (12 g/L), the composition of the production medium was the same as the 1st stage seed medium. Temperature was maintained at 21° C., pH was controlled at 5 with 8N KOH. Aeration at 250 L/min for the first 15 hrs was increased to 300 L/min. Agitation at 150 r.p.m. for the first 15 hrs was increased to 200 r.p.m. A sterilized solution of 70% cerelose, 7% ammonium sulphate was fed incrementally to the fermenter. Specific growth rate of the cells was controlled at about 0.1. When 30 kg of cerelose was fed to the fermenter, the cells were harvested. The cells contained about 1000 ug/g astaxanthin.

Enhancement of Astaxanthin Biosynthesis

It has also been found that when antimycin or another inhibitor of the main respiratory chain are added to *Phaffia rhodozyma* cells, and the cells are exposed to light, the astaxanthin content of the yeast is considerably enhanced. The underlying mechanism for this phenomena is not understood, but it could be hypothesized that when the primary respiratory pathway is inhibited, light acts as one of the triggers of a secondary respiratory (oxidative) pathway, having a net effect of considerably stimulating the production of astaxanthin. Thus, the present invention comprises processes for increasing the astaxanthin or other carotenoid content of yeast, comprising growing the yeast in the presence of a metabolic pathway inhibitor while inducing a secondary respiratory pathway. The secondary respiratory pathway may be induced by such influences as light, certain environmental conditions such as those known to cause stress, nutrients, etc. The present invention is, however, not limited by the above hypothesis.

It will be seen from the experiments discussed below that enhanced astaxanthin biosynthesis can be induced by the above mentioned combination of respiratory chain inhibitor with initiation of the secondary respiratory channel.

EXAMPLE 9

*P. rhodozyma* strains used were the natural isolate UCD-FST-67-385 (Phaff et al., 1972; Miller et al., 1976), mutant Ant-1-4 used above, and strain 18-13-6, an astaxanthin enhanced mutant obtained by ethylmethane sulfonate (EMS) mutagenesis procedures (isolated on YM agar). They were grown in yeast extract/malt extract/peptone/glucose medium (YM medium, Difco Co., Detroit, Mich.) as previously described (An et al., 1989) in a temperature controlled incubator/shaker (Environ-Shaker Model 3597, Lab-Line Instruments, Inc., Melrose Park, Ill.). Growth was determined by the optical density (660 nm) of a washed cell suspension; 1 mg dry cell weight per ml corresponds to an O.D. of 1.35.

Light was supplied by two Sylvania 20 watt Cool-white fluorescent tubes held 20–40 cm from the flask media surfaces. Flasks were inoculated with approximately $10^2 - 10^6$ cells of actively growing yeast. For dark controls, flasks were wrapped in aluminum foil. When insoluble chemicals were included in the media, they were first dissolved in a small quantity of ethanol (0.3% final conc.), which did not affect yeast growth or pigmentation.

Carotenoid Extraction and Analysis

*P. rhodozyma* was grown for 5 days in flasks before extraction. Yeasts were harvested from liquid media by centrifugation. The yeast cells were suspended in distilled water, washed in water, and extracted and analyzed for carotenoids by thin-layer chromatography and absorption spectroscopy as previously described (An et al., 1989).

Secondary Respiratory Pathway Induction Increases Carotenoid Production

The influence of two 20 watt fluorescent bulbs placed 20 cm from the surface of *P. rhodozyma* natural isolate, UCD-FST-67-385, and its antimycin-sensitive mutants, Ant 1-4 and 18-13-6 was studied.

Separate cultures were grown under conditions of (a) total darkness for 30 hours (hereafter "dark"), (b) total darkness with 0.2 μM antimycin (antimycin being introduced at inoculation) (hereafter "dark/antimycin"), and under conditions (c) and (d) which were identical to (a) and (b) except for exposure of the cultures to light from approximately 30 hours into the experiment until approximately 60 hours into the experiment (hereafter "light" and "light/antimycin").

Extraction of the pigments and characterization indicated that the pigments were qualitatively similar in composition, except that more cis-astaxanthin and lower carotene concentrations were found to be present in light grown cells.

Analysis of yeasts showed that the carotenoid content of light/antimycin *P. rhodozyma* UCD-FST-67-385 increased by two-fold over any of the dark, dark/antimycin or light cultures of this natural isolate (Table 1). Table 2 shows that mutant 18-13-6, which is antimycin sensitive, produced two-fold increase in carotenoid content in antimycin/light over the light culture.

TABLE 1

| Conditions | Growth (mg/ml) | Carotenoid (μg/g y) |
|---|---|---|
| Dark | 4.4 | 520 |
| Dark + Ant | 1.6 | 480 |
| Light | 3.3 | 440 |
| Light + Ant | 2.2 | 1000 |

TABLE 2

| Antimycin | Not added | Added |
|---|---|---|
| Light | Carotenoid Content (μg carotenoids/g yeast) | |
| White | 540 | 1410 |
| Blue | 1050 | 1360 |
| Red | 960 | 1210 |
| Dark | 830 | 1013 |

As can be seen from the above results, growth and carotenoid formation of natural and astaxanthin enhanced *P. rhodozyma* is clearly influenced by light. The natural isolate, UCD-FST-67-385, and its antimycin-sensitive mutants ant-1–4 and 18-13-6, each grew better and had increased pigmentation in the dark, but were differently affected by light.

Phaffia as a Food and Pigment Source

The harvested cells can be disrupted or broken using mechanical or enzymatic means or a combination thereof and fed to salmonids, etc. as part of an overall nutritious diet. In order to enhance the stability of astaxanthin in the disrupted or broken yeast against heat and air, it is preferred to provide a protective coating or matrix as conventionally provided in the food art, for example, a natural gum.

Examples wherein *P. rhodozyma* is used as a food supplement for rainbow trout (*Salmo gairdneri*), American lobsters, Coturnix quail, and laying hens are discussed in a Thesis of co-inventor Johnson entitled "Astaxanthin Production by the Yeast *Phaffia rhodozyma* and its use as a Pigment Source in Animal Feeding", Masters Thesis, University of California at Davis, (1976), a copy submitted herewith.

As a consequence of the higher astaxanthin content per unit of cells on a dry basis in the yeast attained according to the present invention, the amount of yeast employed to induce pigmentation can be substantially reduced.

Variations on the design or operation of the above illustrative embodiments may be readily made to adapt the inventive process to various operational demands, all of which are within the scope and spirit of the present invention.

We claim:

1. Phaffia strain IGI887J0.

2. A mutant strain of Phaffia IGI887J0 of claim 1 which produces at least 700 μg of astaxanthin per gram dry weight of Phaffia per six day culture period in YM medium, wherein said astaxanthin is determined by measuring the absorbance at 474 nanometers of a petroleum ether extract of Phaffia using a 1% (w/v) extinction coefficient in a 1 centimeter cuvette of 2100.

3. Phaffia strain IGI887J2.

4. A mutant strain of Phaffia IGI887J2 of claim 3 which produces at least 700 μg of astaxanthin per gram dry weight of Phaffia per six day culture period in YM medium, wherein said astaxanthin is determined by measuring the absorbance at 474 nanometers of a petroleum ether extract of Phaffia using a 1% (w/v) extinction coefficient in a 1 centimeter cuvette of 2100.

* * * * *